US012716353B2

(12) United States Patent
Alshuhail et al.

(10) Patent No.: US 12,716,353 B2
(45) Date of Patent: Aug. 25, 2026

(54) ON SURFACE GAMMA RAY SENSOR FOR CALIBRATING CUTTINGS DEPTH IN UNDERBALANCED COILED TUBING DRILLING RIGS

(71) Applicant: SAUDI ARABIAN OIL COMPANY, Dhahran (SA)

(72) Inventors: Faisal Alshuhail, Dhahran (SA); Abdulrahman Alshuhail, Dhahran (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 130 days.

(21) Appl. No.: 18/398,412

(22) Filed: Dec. 28, 2023

(65) Prior Publication Data

US 2025/0215791 A1 Jul. 3, 2025

(51) Int. Cl.

*E21B 49/00* (2006.01)
*E21B 21/06* (2006.01)
*G01N 33/24* (2006.01)
*G01V 5/06* (2006.01)

(52) U.S. Cl.

CPC ........... *E21B 49/005* (2013.01); *G01N 33/24* (2013.01); *G01V 5/06* (2013.01); *E21B 21/065* (2013.01)

(58) Field of Classification Search

CPC ...... E21B 49/005; E21B 49/00; E21B 49/001; E21B 49/02; E21B 49/025; E21B 49/04; E21B 49/06; E21B 21/06

See application file for complete search history.

(56) References Cited

U.S. PATENT DOCUMENTS 5,068,883 A * 11/1991 DeHaan ................. G01V 5/222 378/197
5,165,275 A * 11/1992 Donovan .............. E21B 49/005 250/254
6,047,784 A * 4/2000 Dorel ...................... E21B 7/068 175/73
6,386,026 B1 * 5/2002 Zamfes ................... E21B 49/02 367/33
10,591,630 B2 3/2020 Berheide et al.

(Continued)

FOREIGN PATENT DOCUMENTS

| | | | |
|---|---|---|---|
| CA | 2861305 | C | 11/2016 |
| WO | 202131388 | A1 | 2/2021 |
| WO | 2021231535 | A1 | 11/2021 |

*Primary Examiner* — Yanick A Akaragwe

(74) *Attorney, Agent, or Firm* — Osha Bergman Watanabe & Burton LLP

(57) ABSTRACT

System and method for on surface calibration of cuttings depth in underbalanced coiled tubing drilling including a drill string for drilling a well and collecting drill cuttings at a first point of a depth interval and at a second point of the depth interval, a gamma ray device at the surface for measuring gamma ray response for drill cuttings at the first point and the second point, and a bottom hole assembly tool on the drill string for measuring downhole gamma readings at a plurality of depths between the first point and the second point of the depth interval. The system further includes an operator on surface for determining a calibration and validation assessment related to the depth interval including a comparison between the gamma ray response and an average of the downhole gamma readings to confirm accuracy of the depth interval of the drill cuttings.

20 Claims, 7 Drawing Sheets

(56) References Cited

U.S. PATENT DOCUMENTS

| | | | | |
|---|---|---|---|---|
| 11,163,088 | B2 | 11/2021 | Kuespert | |
| 11,492,901 | B2 * | 11/2022 | ElGamal | E21B 49/005 |
| 2008/0196942 | A1 * | 8/2008 | Bingham | G01G 11/003<br>175/46 |
| 2013/0270011 | A1 * | 10/2013 | Akkurt | E21B 49/088<br>175/58 |
| 2015/0013448 | A1 * | 1/2015 | Smith | E21B 49/005<br>73/152.46 |
| 2023/0122264 | A1 * | 4/2023 | Ruel | G01N 15/1429<br>382/103 |

* cited by examiner

Data System
Downhole Gamma Readings
220
224
204
208
102
110
216
115
202
116
212
214
218
124
222
210
206

ON SURFACE GAMMA RAY SENSOR FOR CALIBRATING CUTTINGS DEPTH IN UNDERBALANCED COILED TUBING DRILLING RIGS

BACKGROUND

Oil and gas well drilling paths may be affected by many variables in a drilling operation, such as drilling parameters, well parameters, and reservoir parameters. While well paths are often analyzed in the planning stages, unknown factors during a drilling operation may also contribute to dramatic changes in well paths that differ from earlier predictions. During drilling, drill cuttings and drill cuttings depth are essential for steering well path decisions. Currently, the method used for calculating depth of drill cuttings is via a well site drilling engineer calculation based on fluid velocity and measured depth. This method yields inaccurate results in underbalanced coiled tubing drilling (UBCTD) when the wellbore turns into multiphase.

Accordingly, there exists a need for a system and method for validating depth of drill cuttings in UBCTD operations.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In one aspect, embodiments disclosed herein relate to a system for on surface calibration of cuttings depth in underbalanced coiled tubing drilling (UBCTD), the system comprising: a drill string configured to drill a well and collect a plurality of drill cuttings at a first point of a depth interval and at a second point of the depth interval; a gamma ray device disposed at the surface configured to measure a gamma ray response for the plurality of drill cuttings at the first point and the second point of the depth interval; a bottom hole assembly (BHA) tool disposed on the drill string configured to measure a plurality of downhole gamma readings at a plurality of depths between the first point and the second point of the depth interval; and an operator located on surface configured to determine a calibration and validation assessment related to the depth interval, the calibration and validation assessment comprising a comparison between the gamma ray response and an average of the plurality of downhole gamma readings to confirm accuracy of the depth interval of the plurality of drill cuttings.

In one aspect, embodiments disclosed herein relate to a method for calibrating and validating depth of cuttings from a well, the method comprising: drilling the well using a drill string comprising a bottom hole assembly (BHA) tool; collecting while drilling the well, via the drill string, a plurality of drill cuttings from a first point of a depth interval and a second point of the depth interval; measuring a gamma ray response for the plurality of drill cuttings at the first point and the second point using a gamma ray device disposed on surface; measuring a plurality of downhole gamma readings at a plurality of depths between the first point and the second point of the depth interval using the BHA tool; and determining a calibration and validation assessment related to the depth interval, the calibration and validation assessment comprising a comparison between the gamma ray response and an average of the plurality of downhole gamma readings to confirm accuracy of the depth interval of the plurality of drill cuttings.

Other aspects and advantages of the claimed subject matter will be apparent from the following description and the appended claims.

DETAILED DESCRIPTION

Figure 1:
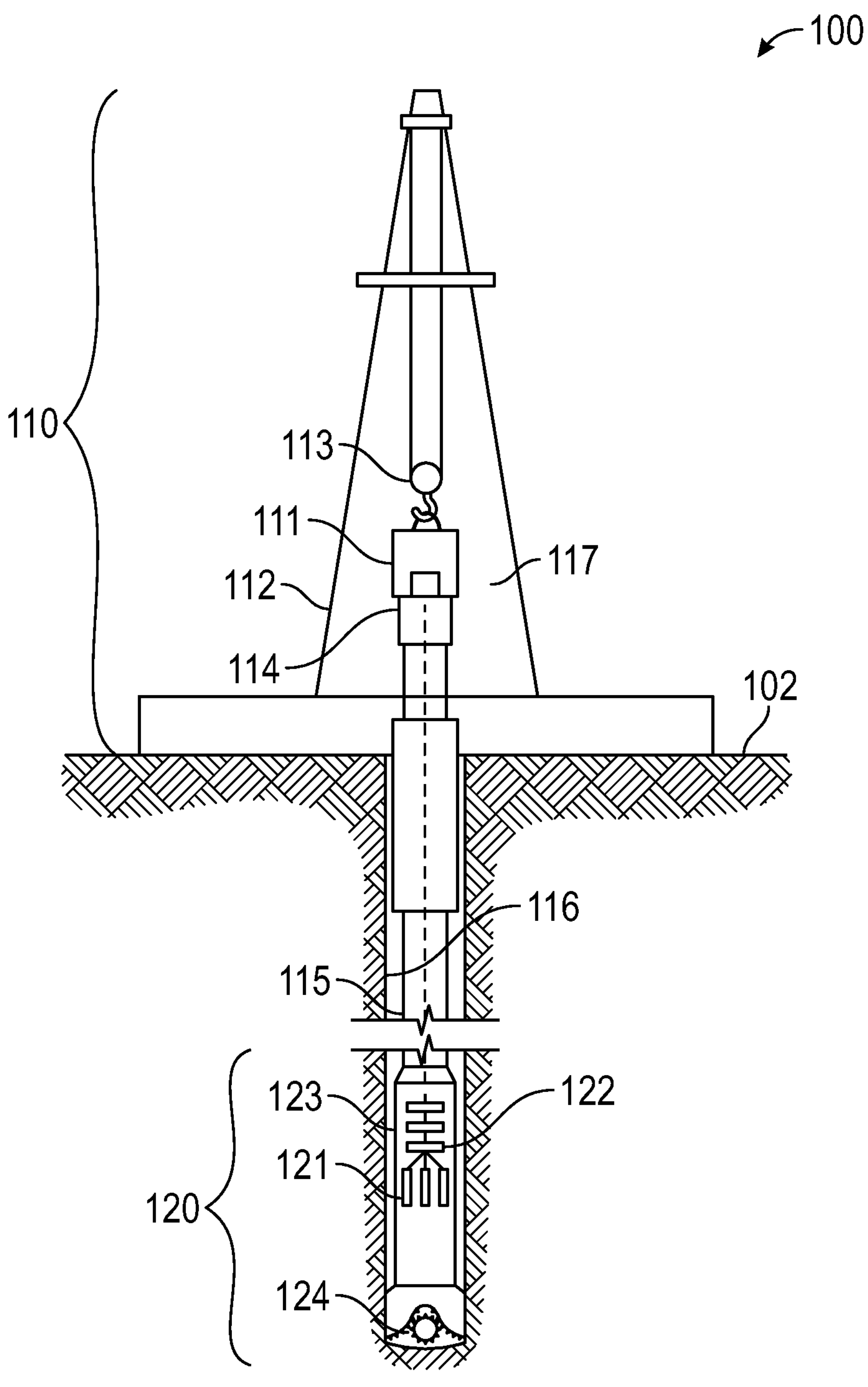
FIG. 1 shows a well system in accordance with one or more embodiments.

In the following detailed description of embodiments of the disclosure, numerous specific details are set forth in order to provide a more thorough understanding of the disclosure. However, it will be apparent to one of ordinary skill in the art that the disclosure may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers is not to imply or create any particular ordering of the elements nor to limit any element to being only a single element unless expressly disclosed, such as using the terms "before," "after," "single," and other such terminology. Rather, the use of ordinal numbers is to distinguish between the elements. By way of an example, a first element is distinct from a second element, and the first element may encompass more than one element and succeed (or precede) the second element in an ordering of elements.

In the following description of FIGS. 1-7, any component described regarding a figure, in various embodiments disclosed herein, may be equivalent to one or more like-named components described with regard to any other figure. For brevity, descriptions of these components will not be repeated regarding each figure. Thus, each and every embodiment of the components of each figure is incorporated by reference and assumed to be optionally present within every other figure having one or more like-named components. Additionally, in accordance with various embodiments disclosed herein, any description of the components of a figure is to be interpreted as an optional embodiment which may be implemented in addition to, in conjunction with, or in place of the embodiments described with regard to a corresponding like-named component in any other figure.

It is to be understood that the singular forms "a," "an," and "the" include plural referents unless the context clearly dictates otherwise. Thus, for example, reference to "a force applicator" includes reference to one or more of such force applicators.

Regarding the figures described herein, when using the term "down" the direction is toward or at the bottom of a respective figure and "up" is toward or at the top of the respective figure. "Up" and "down" are oriented relative to a local vertical direction. However, in the oil and gas industry, one or more activities take place in a vertical, substantially vertical, deviated, substantially horizontal, or horizontal well. Therefore, one or more figures may represent an activity in deviated or horizontal wellbore configuration. "Uphole" may refer to objects, units, or processes that are positioned relatively closer to the surface entry in a wellbore than another. "Downhole" may refer to objects, units, or processes that are positioned relatively farther from the surface entry in a wellbore than another. Measured depth (MD) is the length of the wellbore. True vertical depth (TVD) is the vertical distance from a point in the well at a location of interest to a reference point on the surface.

Underbalanced Coiled Tubing Drilling (UBCTD) technology is used to develop mature and depleted reservoirs. Underbalanced drilling (UBCTD) involves drilling while keeping the pressure of the wellbore lower than the static pressure of the formation being drilled. Traditional UBCTD practice only accommodates gamma ray devices or tools in terms of formation tools due to the slim-hole nature of coiled tubing bottom hole assemblies (BHA). Slim-hole coiled tubing BHAs, around 3.5 inches in diameter, limit the addition of larger tools such as neutron density, porosity, sonic, etc.

Typically, an operation geologist is present at the site to help steer UBCTD laterals by examining drill cuttings. The operation geologist examines drill cuttings extracted by a well site drilling engineer (WSDE) during drilling operations based on characteristic properties. The operation geologist then makes steering decisions based on the examination by inferring on the stratigraphic position of the BHA. The operation geologist instructs a directional driller (DD) at the drill site of the steering decisions to adjust lateral well path position accordingly. Therefore, it is crucial with steering decisions that the depths of the drill cuttings examined be accurate. The WSDE may be responsible for hole cleaning and coordinating with surface facility crew to collect drill cutting samples.

Typically, labeling the depth of the collected drill cuttings is based on a WSDE calculation. The WSDE calculation is based on the velocity of fluids within the wellbore and the MD to yield the expected time for the drill cuttings to reach surface and be collected. The expected time for drill cuttings to reach surface for collection is referred to as "bottoms up time". The WSDE calculation is inaccurate in UBCTD because the process does not consider possible contamination of the drill cuttings from previously drilled sections, especially when the well conditions alter from single phase overbalance conditions to multiphase underbalance conditions. When well conditions change from single phase to multiphase, fluid velocity estimation is difficult to calculate. Fluid velocity miscalculation leads to misrepresentation of depth in drill cuttings. The misrepresentation of drill cuttings depth leads to incorrect lateral placement decisions made by the geologist.

In one aspect, embodiments disclosed herein relate to a system for on surface calibration of cuttings depth in UBCTD. The system provides a method for validating and calibrating the depth of drill cuttings during UBCTD. The system includes a gamma ray device used on surface to calibrate cuttings depth extracted from drilling operations with their respective depth downhole. The gamma ray device measures the gamma ray responses of the drill cuttings from a particular depth range. The system further includes a gamma ray tool in the BHA to measure downhole gamma readings in the same particular depth range. The gamma ray responses and the downhole gamma readings are then cross referenced for calibration by an operator or geologist. The calibration indicates to the operator whether any contamination or caving from a previously drilled section is present that would cause misinterpretation when logging drill cuttings samples.

Turning to FIG. 1, FIG. 1 illustrates a system in accordance with one or more embodiments. As shown in FIG. 1, a drilling system (100) may be located on a ground surface (e.g., a surface (102)) include a top drive drill rig (110) arranged around the setup of a drill bit logging tool (120). A top drive drill rig (110) may include a top drive (111) that may be suspended in a derrick (112) by a travelling block (113). In the center of the top drive (111), a drive shaft (114) may be coupled to a top pipe of a drill string (115), for example, by threads. The top drive (111) may rotate the drive shaft (114), so that the drill string (115) and a drill bit logging tool (120) cut the rock at the bottom of a wellbore (116). A power cable (117) supplying electric power to the top drive (111). As such, drilling fluid may be pumped into the wellbore (116) using the drive shaft (114) and/or the drill string (115). Likewise, the drilling system may also include a mud pump, a mud line, mud pits, a mud return, and other components related to the circulation or recirculation of drilling fluid within the wellbore (116).

In some embodiments, the drilling system (100) includes a bottomhole assembly (BHA). The bottomhole assembly may refer to a lower portion of the drill string (115) that includes a drill bit (124), bit sub (i.e., a substitute adapter), and a drill collar. The bottomhole assembly may also include a mud motor, stabilizers, heavy-weight drill pipe, jarring devices ("jars"), crossovers for various threadforms, directional drilling and measuring equipment, measurements-while-drilling tools, logging-while-drilling tools, and other specialized devices. The bottomhole assembly may produce force for the drill bit to break rock and provide the drilling system with directional control of a wellbore. Different types of bottomhole assemblies may be used, such as a rotary assembly, a fulcrum assembly, and a pendulum assembly.

Moreover, when completing a well, casing may be inserted into the wellbore (116). The sides of the wellbore (116) may require support, and thus the casing may be used for supporting the sides of the wellbore (116). As such, a space between the casing and the untreated sides of the wellbore (116) may be cemented to hold the casing in place. The cement may be forced through a lower end of the casing and into an annulus between the casing and a wall of the wellbore (116). More specifically, a cementing plug may be used for pushing the cement from the casing. For example, the cementing plug may be a rubber plug used to separate cement slurry from other fluids, reducing contamination and maintaining predictable slurry performance. A displacement fluid, such as water, or an appropriately weighted drilling fluid, may be pumped into the casing above the cementing plug. This displacement fluid may be pressurized fluid that serves to urge the cementing plug downward through the casing to extrude the cement from the casing outlet and back up into the annulus.

As further shown in FIG. 1, sensors (121) may be included in a sensor assembly (123), which is positioned adjacent to a drill bit (124) and coupled to the drill string (115). Sensors (121) may also be coupled to a processor assembly that includes a processor, memory, and an analog-to-digital converter (122) for processing sensor measurements. For example, the sensors (121) may include acoustic sensors, such as accelerometers, measurement microphones, contact microphones, and hydrophones. Likewise, the sensors (121) may include other types of sensors, such as transmitters and receivers to measure resistivity, gamma ray detectors, etc. The sensors (121) may include hardware and/or software for generating different types of well logs (such as acoustic logs or density logs) that may provide well data about a wellbore, including porosity of wellbore sections, gas saturation, bed boundaries in a geologic formation, fractures in the wellbore or completion cement, and many other pieces of information about a formation. If such well data is acquired during drilling operations (i.e., logging-while-drilling), then the information may be used to make adjustments to drilling operations in real-time. Such adjustments may include rate of penetration (ROP), drilling direction, altering mud weight, and many others drilling parameters.

In accordance with one or more embodiments the drill string (115) may comprise a coiled tubing. Coiled tubing may be wound on a spool prior to drilling the wellbore (116) and is straightened for pushing into the wellbore. The drill string comprises the drill bit that is disposed at a downhole end of the drill string. The drill bit drills the wellbore into the formation. The wellbore may run diagonally in an upper section close to the ground surface and horizontally in a lower section distant from the ground surface.

The drilling parameters include, amongst others, rate of penetration (ROP), weight on bit (WOB), mud weight, and other associated parameters. The drilling parameters play a crucial role in determining the formation and providing implicit information on the geomechanics of the formation, and indirectly on its porosity. The well parameters incorporate the production performance, such as gas production, the well length and trajectory, net-to-gross ratio, formation intersections, TVD, and MD in addition to completion parameters. Furthermore, several reservoir parameters are sourced from the reservoir environment, which may include reservoir geology, bio-steering derived information, as well as drill cuttings provided information.

Figure 2:
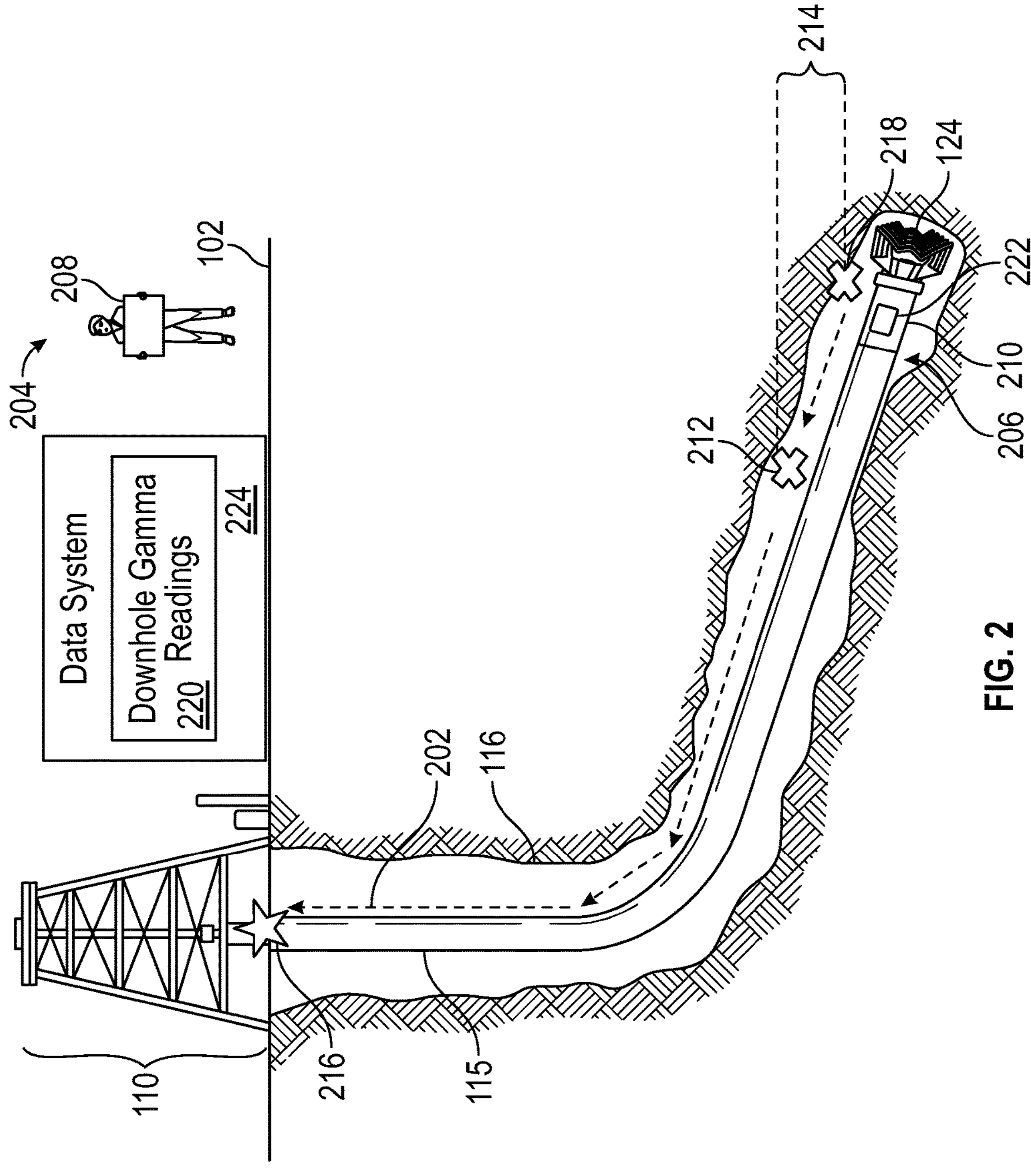
FIG. 2 shows a system in accordance with one or more embodiments.

FIG. 2 shows a system for on surface calibration of cuttings depth in UBCTD in accordance with one or more embodiments. Specifically, FIG. 2 illustrates a surface calibration of cuttings depth system that may be used in conjunction with FIG. 1. Cuttings depth refers to the depth assigned to collected drill cuttings (202). In UBCTD drilling, the wellbore (116) may be a lateral well as illustrated in FIG. 2. Drill cutting samples or drill cuttings (202) may be collected in intervals, such as every 10 feet or every hour. The drill cuttings (202) may be extracted by a well site drilling engineer (WSDE) and given to an operator (204) or operation geologist for examination. The operator (204) may then make steering decisions for drilling based on the examination by inferring on the stratigraphic position of the BHA (206) as described in FIG. 1. A directional driller or WSDE may then adjust the lateral well path position accordingly. Therefore, it is crucial with steering decisions that cuttings depth is accurate and calibrated. The surface calibration of cuttings depth system shown in FIG. 2 may be used to calibrate and validate cuttings depth during drilling.

The surface calibration of cuttings depth system includes the drill string (115), a gamma ray device (208), a BHA tool (210), and the operator (204). As described in FIG. 1, the drill string (115) drills the well or wellbore (116). As the drill string (115) drills at a certain depth, drill cuttings (202) are collected at that depth. For example, as illustrated in FIG. 2, drill cuttings (202) are collected at a first point (212) of a depth interval (214). The drill cuttings (202) from the first point (212) are collected and transported to a collection point (216) at the surface (102), as indicated by the arrows shown in FIG. 2. Drill cuttings (202) may have a lag time of about 20 to 40 minutes during travel to be collected at surface (102). Drill cuttings (202) are then collected at a second point (218) of the same depth interval (214). The depth interval (214) may be 10 feet. The drill cuttings (202) from the second point (218) are collected at the collection point (216) on surface (102) similarly to the drill cuttings (202) from the first point (212).

The drill cuttings (202) from the first point (212) and the second point (218) are put under the gamma ray device (208) on surface (102). The operator (204) measures gamma ray response of the drill cuttings (202) using the gamma ray device (208). The operator (204) may be a geologist in a laboratory. The gamma ray responses may be documented and stored, such as in a computer system (702) further described in FIG. 7.

The BHA tool (210) may be installed in the BHA (206) to measure downhole gamma readings (220). The BHA tool (210) may include a formation gamma ray response tool (222). The formation gamma ray response tool (222) may measure continuous data of the downhole gamma readings (220). The BHA tool (210) measures downhole gamma readings (220) at multiple depths in the depth interval (214), such as every 0.5 ft, between the first point (212) and the second point (218). The BHA tool (210) may transmit the downhole gamma readings (220) to the data system (224) on surface (102). The data system (224) may be the computer system (702) further described in FIG. 7. The operator (204) may use the data system (224) to observe both the downhole gamma readings (220) and the gamma ray responses at each depth. The operator (204) may then determine a calibration and validation assessment regarding the depth interval by comparing the average downhole gamma reading to the gamma ray responses to confirm the accuracy of the depth interval (214). The operator (204) may cross-reference the average downhole gamma reading and the gamma ray responses to determine the calibration and validation assessment.

Figure 3:
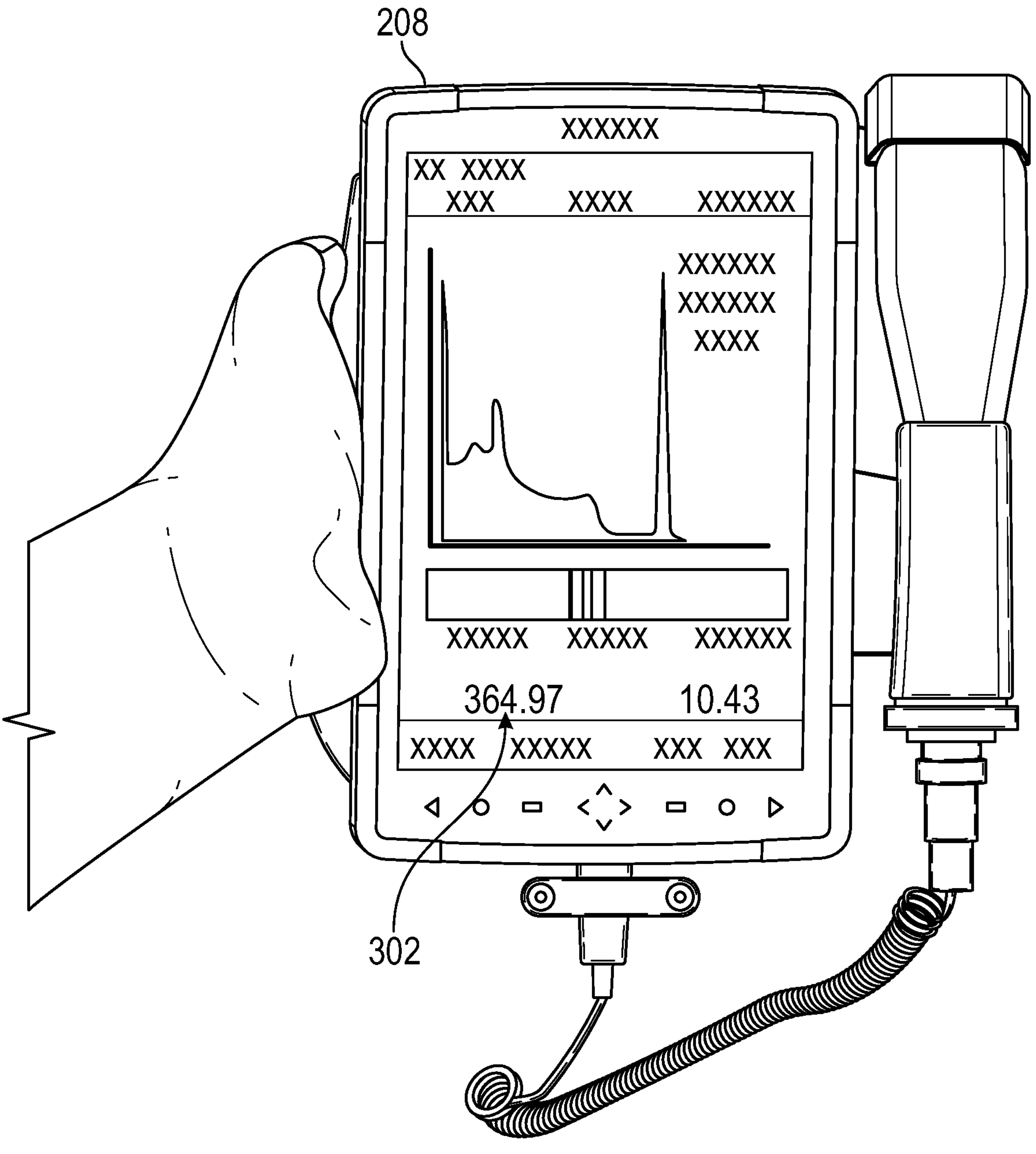
FIG. 3 shows a gamma ray device in accordance with one or more embodiments.

FIG. 3 shows a gamma ray device (208) in accordance with one or more embodiments. A person or ordinary skill in the art would appreciate that the gamma ray device (208) may be a handheld device. The gamma ray device (208) may include a display or user interface for showing measurements of gamma ray response (302). The gamma ray device (208) may have the capability of connecting to the computer system (702), further described in FIG. 7, for analysis or data storing.

Figure 4:
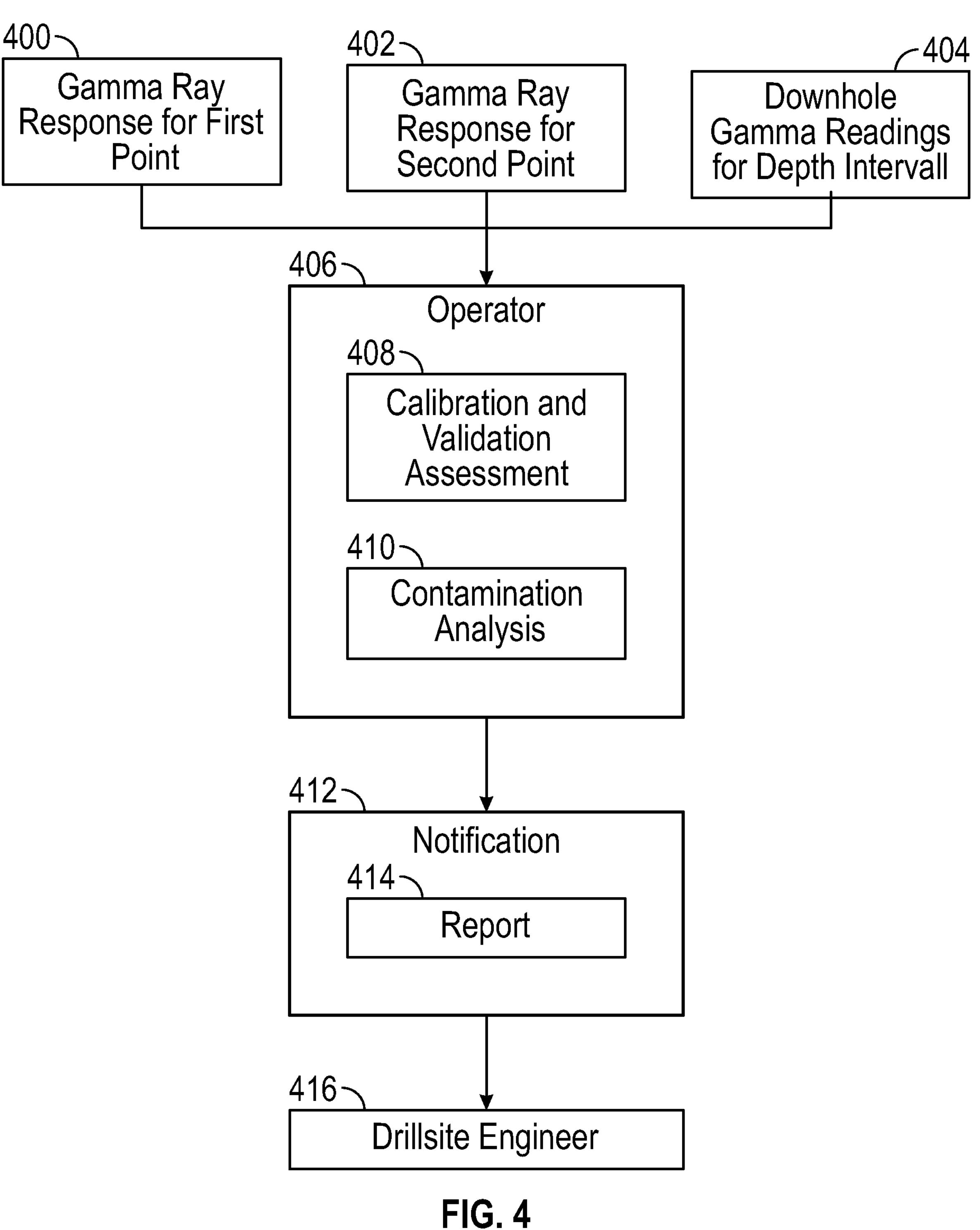
FIG. 4 shows a diagram in accordance with one or more embodiments.

FIG. 4 shows a diagram in accordance with one or more embodiments. Specifically, FIG. 4 shows example methodology for the surface calibration of cuttings depth system described in FIG. 2. In one or more embodiments, a gamma ray response for a first point (400), a gamma ray response for a second point (402), and downhole gamma readings for a depth interval (404) are collected and received by an operator (406). As described in FIG. 2, the gamma ray response for the first point (400) is the measured gamma ray response by the gamma ray device at the first point of a depth interval. Accordingly, the gamma ray response for the second point (402) is the measured gamma ray response by the gamma ray device at the second point of the same depth interval. The downhole gamma readings for the depth interval (404) are the downhole gamma readings measured by the BHA tool.

The operator (406) then uses the gamma ray response for the first point (400), the gamma ray response for the second point (402), and the downhole gamma readings for the depth interval (404) to determine a calibration and validation assessment (408). The calibration and validation assessment (408) represents the comparison between the gamma ray responses and the average of the downhole gamma readings to confirm the accuracy of cuttings depth or the depth interval of the drill cuttings. The operator may further perform a contamination analysis (410) of the drill cuttings based on the calibration and validation assessment (408). The contamination analysis (410) represents if the drill cuttings sample has been contaminated. For example, contamination of drill cuttings may occur from a result of underlying hole cleaning issues, such as drill cuttings accumulation along the lateral profile of the wellbore.

The operator (204) may then send or transmit a notification (412) to a drill site engineer (416). The notification (412) includes a report (414) indicating any potential underlying hole cleaning issue identified in the contamination analysis (410).

Figure 5:
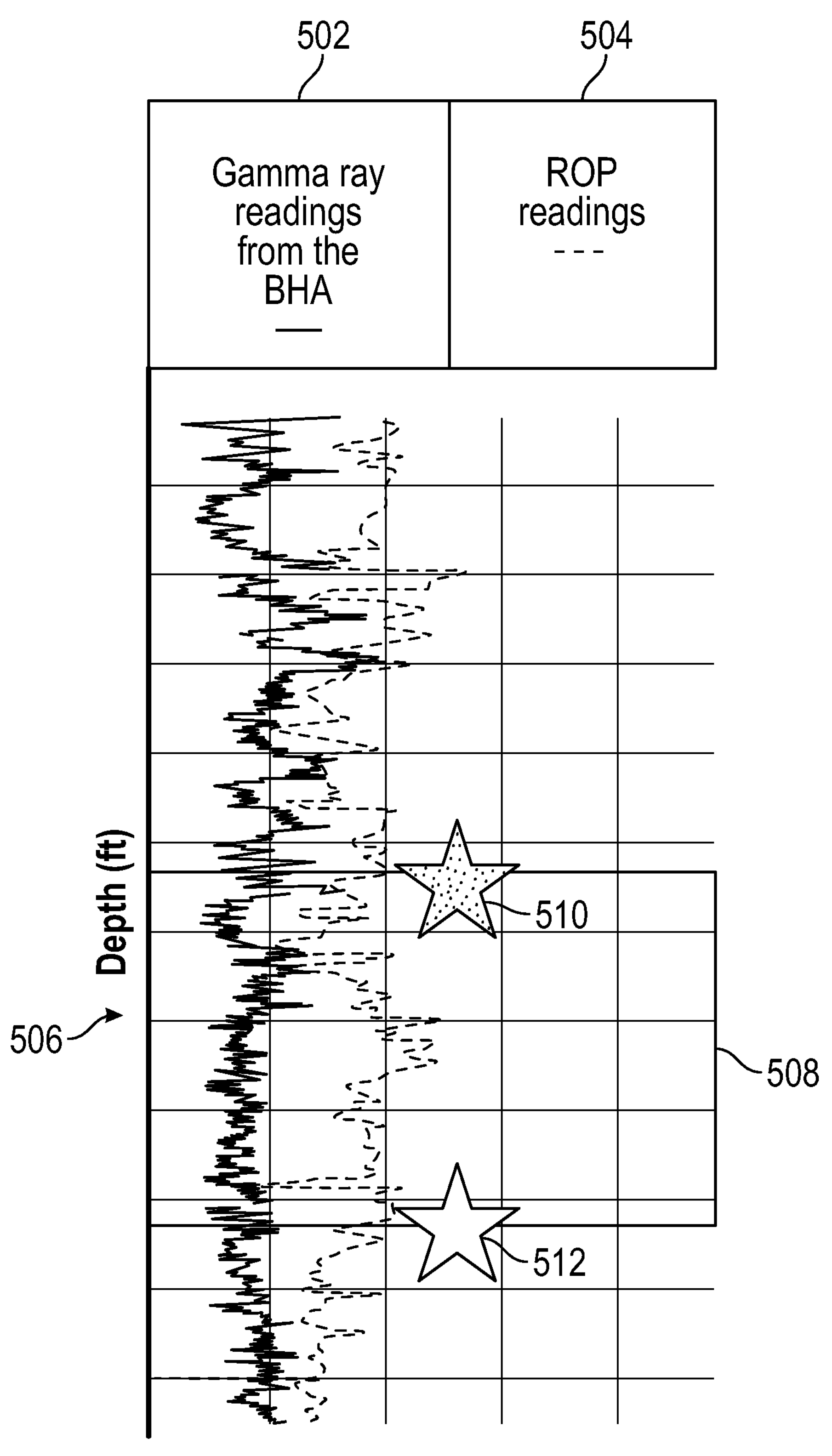
FIG. 5 shows a graphical analysis in accordance with one or more embodiments.

FIG. 5 shows a graphical analysis in accordance with one or more embodiments. Specifically, FIG. 5 illustrates an example of what an operator would analyze and cross reference after collecting gamma ray responses, downhole gamma readings (502), and rate of penetration (ROP) readings (504). The data in the graphical analysis is represented at a plurality of depths in feet, as shown by the Y axis (506). The downhole gamma readings (502) are shown as a solid line in the graphical analysis. The ROP readings (504) are shown by the dotted line in the graphical analysis. A box surrounding the data in the graphical analysis represents a specific depth interval (508) of 10 ft between two points (e.g., first point (212) and second point (218)). In this example, the depth interval (508) is between 13000 feet MD and 13010 feet MD. The dotted star (510) represents the gamma ray response at 13000 ftMD. The solid star (512) represents the gamma ray response at 13010 ftMD.

The operator may cross reference the gamma responses for the two points (e.g., dotted start (510) and solid star (512)), downhole gamma readings (502) within the depth interval (508), and rate of penetration (ROP) readings (504) within the same depth interval (508). The gamma ray responses (510, 512) are measurements made by a gamma ray device for collected drill cuttings. The downhole gamma readings (502) are measured by a BHA tool during drilling. The ROP readings (504) represent the speed at which a drill bit in a BHA drills a wellbore. In FIG. 5, the ROP readings (504) specifically refer to the speeds in the depth interval.

If the cross reference indicates that the values of the downhole gamma readings (502) and the gamma ray responses (510, 512) are not similar, then the drill cuttings collected sample may be contaminated. The operator may document the specific drill cuttings sample that is contaminated. The operator then takes extra caution when interpreting the contaminated drill cuttings sample. The operator may notify the WSDE that there may be hole cleaning issues that have caused the contaminated sample. If the cross reference indicates similarity in the values, then no contamination is present.

Figure 6:
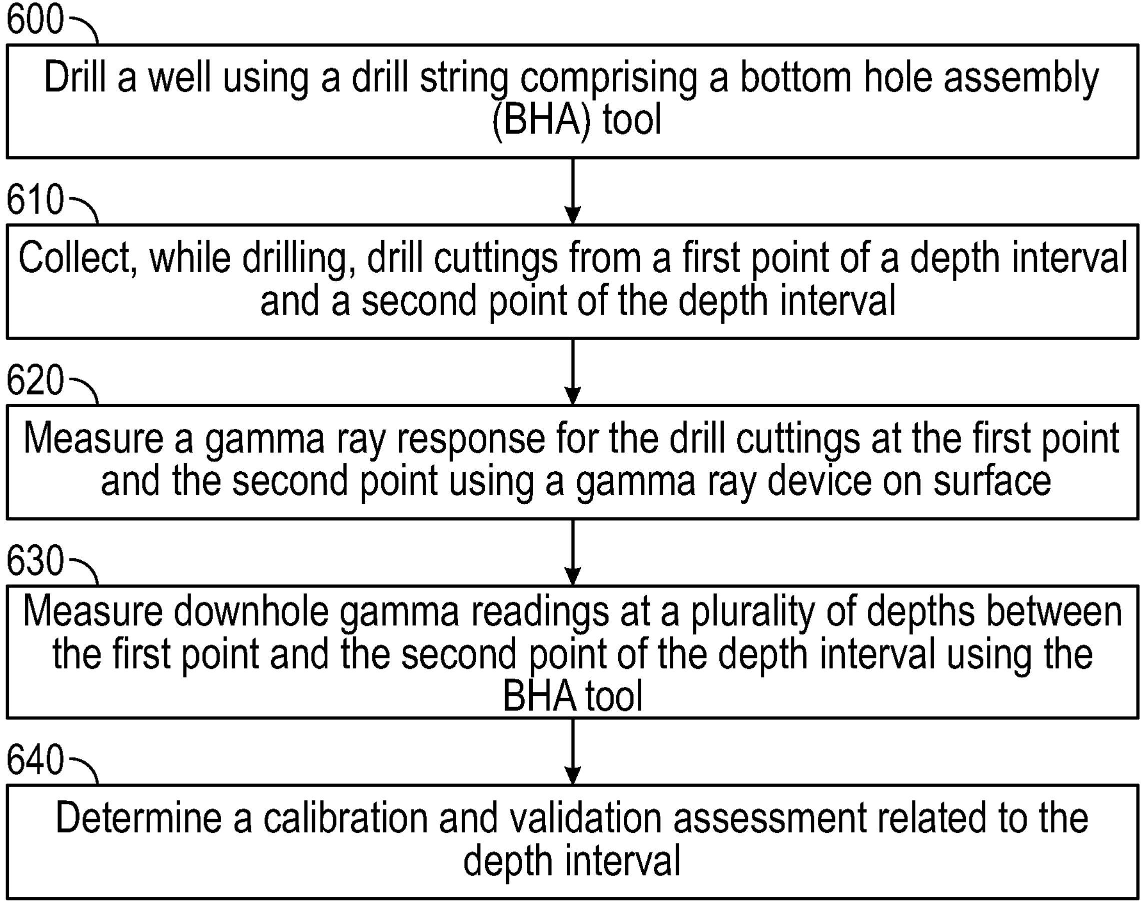
FIG. 6 shows a flowchart in accordance with one or more embodiments.

FIG. 6 shows a flowchart in accordance with one or more embodiments. Specifically, FIG. 6 describes a general method for calibrating and validating depth of cuttings from a well. The general method may be implemented to a variety of wells during drilling, such as UBCTD. One or more blocks in FIG. 6 may be performed by one or more components (e.g., a gamma ray device (208) and a BHA tool (210)) as described in FIG. 2. While various blocks in FIG. 6 are presented and described sequentially, one of ordinary skill in the art will appreciate that some or all of the blocks may be executed in different orders, may be combined or omitted, and some or all of the blocks may be executed in parallel. Furthermore, the blocks may be performed actively or passively.

In Block 600, a well is drilled using a drill string comprising a bottom hole assembly (BHA) tool. In Block 610, while drilling, drill cuttings are collected from a first point of a depth interval and a second point of the depth interval. A cuttings sample every 10 feet may be collected when the drill cuttings are collected. The drill cuttings may be processed by an operator for proper acquisition. In Block 620, a gamma ray response for the drill cuttings at the first point and the second point are measured using a gamma ray device on surface. Natural radioactivity of the drill cuttings may be measured for the gamma ray response. The gamma ray device may be portable.

In Block 630, downhole gamma readings at a plurality of depths between the first point and the second point of the depth interval are measured using the BHA tool. Continuous data may be measured from a formation gamma response tool in the BHA tool. The downhole gamma readings may be measured every 0.5 ft. In Block 640, a calibration and validation assessment related to the depth interval is determined. The calibration and validation assessment includes a comparison between the gamma ray response and an average of the downhole gamma readings. The comparison is used to confirm accuracy of the depth interval of the drill cuttings. The downhole gamma readings may be extracted for the calibration and validation assessment using a software or computer system as further described in FIG. 7. A contamination analysis of the drill cuttings may be detected using the calibration and validation assessment. An operator may notify a drillsite engineer of a potential underlying hole cleaning issue based, at least in part, on the contamination analysis.

Figure 7:
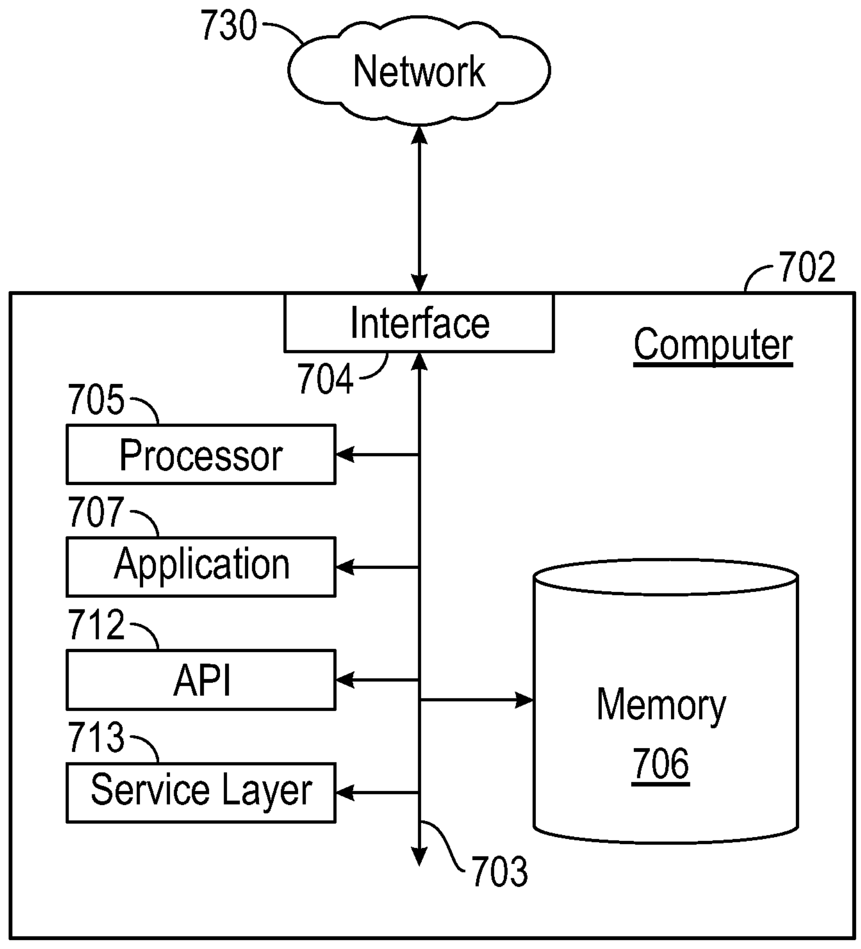
FIG. 7 shows a computer system in accordance with one or more embodiments.

Embodiments may be implemented on a computer system. FIG. 7 is a block diagram of a computer system (702) used to provide computational functionalities associated with described algorithms, methods, functions, processes, flows, and procedures as described in the instant disclosure, according to an implementation. The illustrated computer (702) is intended to encompass any computing device such as a high performance computing (HPC) device, a server, desktop computer, laptop/notebook computer, wireless data port, smart phone, personal data assistant (PDA), tablet computing device, one or more processors within these devices, or any other suitable processing device, including both physical or virtual instances (or both) of the computing device. Additionally, the computer (702) may include a computer that includes an input device, such as a keypad, keyboard, touch screen, or other device that can accept user information, and an output device that conveys information associated with the operation of the computer (702), including digital data, visual, or audio information (or a combination of information), or a GUI.

The computer (702) can serve in a role as a client, network component, a server, a database or other persistency, or any other component (or a combination of roles) of a computer system for performing the subject matter described in the instant disclosure. The illustrated computer (702) is communicably coupled with a network (730). In some implementations, one or more components of the computer (702) may be configured to operate within environments, including cloud-computing-based, local, global, or other environment (or a combination of environments).

At a high level, the computer (702) is an electronic computing device operable to receive, transmit, process, store, or manage data and information associated with the described subject matter. According to some implementations, the computer (702) may also include or be communicably coupled with an application server, e-mail server, web server, caching server, streaming data server, business intelligence (BI) server, or other server (or a combination of servers).

The computer (702) can receive requests over network (730) from a client application (for example, executing on another computer (702)) and responding to the received requests by processing the said requests in an appropriate software application. In addition, requests may also be sent to the computer (702) from internal users (for example, from a command console or by other appropriate access method), external or third-parties, other automated applications, as well as any other appropriate entities, individuals, systems, or computers.

Each of the components of the computer (702) can communicate using a system bus (703). In some implementations, any or all of the components of the computer (702), both hardware or software (or a combination of hardware and software), may interface with each other or the interface (704) (or a combination of both) over the system bus (703) using an application programming interface (API) (712) or a service layer (713) (or a combination of the API (712) and service layer (713). The API (712) may include specifications for routines, data structures, and object classes. The API (712) may be either computer-language independent or dependent and refer to a complete interface, a single function, or even a set of APIs. The service layer (713) provides software services to the computer (702) or other components (whether or not illustrated) that are communicably coupled to the computer (702). The functionality of the computer (702) may be accessible for all service consumers using this service layer. Software services, such as those provided by the service layer (713), provide reusable, defined business functionalities through a defined interface. For example, the interface may be software written in JAVA, C++, or other suitable language providing data in extensible markup language (XML) format or other suitable format. While illustrated as an integrated component of the computer (702), alternative implementations may illustrate the API (712) or the service layer (713) as stand-alone components in relation to other components of the computer (702) or other components (whether or not illustrated) that are communicably coupled to the computer (702). Moreover, any or all parts of the API (712) or the service layer (713) may be implemented as child or sub-modules of another software module, enterprise application, or hardware module without departing from the scope of this disclosure.

The computer (702) includes an interface (704). Although illustrated as a single interface (704) in FIG. 7, two or more interfaces (704) may be used according to particular needs, desires, or particular implementations of the computer (702). The interface (704) is used by the computer (702) for communicating with other systems in a distributed environment that are connected to the network (730). Generally, the interface (includes logic encoded in software or hardware (or a combination of software and hardware) and operable to communicate with the network (730). More specifically, the interface (704) may include software supporting one or more communication protocols associated with communications such that the network (730) or interface's hardware is operable to communicate physical signals within and outside of the illustrated computer (702).

The computer (702) includes at least one computer processor (705). Although illustrated as a single computer processor (705) in FIG. 7, two or more processors may be used according to particular needs, desires, or particular implementations of the computer (702). Generally, the computer processor (705) executes instructions and manipulates data to perform the operations of the computer (702) and any algorithms, methods, functions, processes, flows, and procedures as described in the instant disclosure.

The computer (702) also includes a memory (706) that holds data for the computer (702) or other components (or a combination of both) that can be connected to the network (730). For example, memory (706) can be a database storing data consistent with this disclosure. Although illustrated as a single memory (706) in FIG. 7, two or more memories may be used according to particular needs, desires, or particular implementations of the computer (702) and the described functionality. While memory (706) is illustrated as an integral component of the computer (702), in alternative implementations, memory (706) can be external to the computer (702).

The application (707) is an algorithmic software engine providing functionality according to particular needs, desires, or particular implementations of the computer (702), particularly with respect to functionality described in this disclosure. For example, application (707) can serve as one or more components, modules, applications, etc. Further, although illustrated as a single application (707), the application (707) may be implemented as multiple applications (707) on the computer (702). In addition, although illustrated as integral to the computer (702), in alternative implementations, the application (707) can be external to the computer (702).

There may be any number of computers (702) associated with, or external to, a computer system containing computer (702), each computer (702) communicating over network (730). Further, the term "client," "user," and other appropriate terminology may be used interchangeably as appropriate without departing from the scope of this disclosure. Moreover, this disclosure contemplates that many users may use one computer (702), or that one user may use multiple computers (702).

In some embodiments, the computer (702) is implemented as part of a cloud computing system. For example, a cloud computing system may include one or more remote servers along with various other cloud components, such as cloud storage units and edge servers. In particular, a cloud computing system may perform one or more computing operations without direct active management by a user device or local computer system. As such, a cloud computing system may have different functions distributed over multiple locations from a central server, which may be performed using one or more Internet connections. More specifically, cloud computing system may operate according to one or more service models, such as infrastructure as a service (IaaS), platform as a service (PaaS), software as a service (Saas), mobile "backend" as a service (MBaaS), serverless computing, artificial intelligence (AI) as a service (AIaaS), and/or function as a service (FaaS).

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims.

What is claimed:

1. A system for on surface calibration of cuttings depth in underbalanced coiled tubing drilling (UBCTD), the system comprising:

a drill string configured to drill a well and collect a plurality of drill cuttings at a first point and at a second point defining a depth interval therebetween selected for calibration, wherein the depth interval comprises a predetermined interval length selected for validation of cuttings depth accuracy;

a gamma ray device disposed at the surface configured to measure a gamma ray response for the plurality of drill cuttings at the first point and the second point of the depth interval;

a bottom hole assembly (BHA) tool disposed on the drill string configured to measure a plurality of downhole gamma readings over a plurality of depths spanning the depth interval between the first point and the second point; and an operator located on surface configured to determine a calibration and validation assessment related to the depth interval, the calibration and validation assessment comprising a comparison between the gamma ray response at the first point and the second point and an average of the plurality of downhole gamma readings measured within the depth interval to confirm accuracy of the depth interval of the plurality of drill cuttings.

2. The system of claim 1, further comprising:

a contamination analysis of the plurality of drill cuttings based, at least in part, on the calibration and validation assessment.

3. The system of claim 2, further comprising:

a notification, from the operator to a drill site engineer, comprising a report indicating a potential underlying hole cleaning issue based, at least in part, on the contamination analysis.

4. The system of claim 1, wherein the plurality of drill cuttings comprises a collection of cuttings samples every 10 feet.

5. The system of claim 1, wherein the gamma ray response is a natural radioactivity measurement of the plurality of drill cuttings.

6. The system of claim 1, wherein the plurality of downhole gamma readings comprises continuous data from a formation gamma response tool in the BHA tool.

7. The system of claim 1, wherein the calibration and validation assessment comprises an extraction of the plurality of downhole gamma readings using a software.

8. The system of claim 1, wherein the gamma ray device is portable.

9. The system of claim 1, wherein a geologist is configured to process the plurality of drill cuttings for proper acquisition.

10. The system of claim 1, wherein the plurality of downhole gamma readings comprises of a plurality of measurements every 0.5 feet.

11. A method for calibrating and validating depth of cuttings from a well, the method comprising:

drilling the well using a drill string comprising a bottom hole assembly (BHA) tool;

collecting while drilling the well, via the drill string, a plurality of drill cuttings from a first point and a second point defining a depth interval therebetween selected for calibration, wherein the depth interval comprises a predetermined interval length selected for validation of cuttings depth accuracy;

measuring a gamma ray response for the plurality of drill cuttings at the first point and the second point using a gamma ray device disposed on surface;

measuring a plurality of downhole gamma readings over a plurality of depths spanning the depth interval between the first point and the second point using the BHA tool; and determining a calibration and validation assessment related to the depth interval, the calibration and validation assessment comprising a comparison between the gamma ray response at the first point and the second point and an average of the plurality of downhole gamma readings measured within the depth interval to confirm accuracy of the depth interval of the plurality of drill cuttings.

12. The method of claim 11, further comprising:

detecting, via the calibration and validation assessment, a contamination analysis of the plurality of drill cuttings.

13. The method of claim 12, further comprising:

notifying, via an operator, a drillsite engineer of a potential underlying hole cleaning issue based, at least in part, on the contamination analysis.

14. The method of claim 11, wherein collecting the plurality of drill cuttings comprises collecting a cuttings sample every 10 feet.

15. The method of claim 11, wherein measuring the gamma ray response comprises measuring natural radioactivity of the plurality of drill cuttings.

16. The method of claim 11, wherein measuring the plurality of downhole gamma readings comprises measuring continuous data from a formation gamma response tool in the BHA tool.

17. The method of claim 11, wherein determining the calibration and validation assessment comprises extracting the plurality of downhole gamma readings using a software.

18. The method of claim 11, wherein the gamma ray device is portable.

19. The method of claim 11, wherein collecting the plurality of drill cuttings comprises processing the plurality of drill cuttings by an operator for proper acquisition.

20. The method of claim 11, wherein measuring the plurality of downhole gamma readings comprises measuring the plurality of downhole gamma readings every 0.5 feet.

* * * * *